United States Patent [19]

Bouma et al.

[11] Patent Number: 5,585,242

[45] Date of Patent: Dec. 17, 1996

[54] METHOD FOR DETECTION OF NUCLEIC ACID USING TOTAL INTERNAL REFLECTANCE

[75] Inventors: Stanley R. Bouma, Grayslake; Omar S. Khalil, Libertyville; Edward K. Pabich, Chicago, all of Ill.

[73] Assignee: Abbott Laboratories, Abbott Park, Ill.

[21] Appl. No.: 522,623

[22] Filed: Aug. 31, 1995

Related U.S. Application Data

[63] Continuation of Ser. No. 311,839, Sep. 23, 1994, abandoned, which is a continuation of Ser. No. 863,553, Apr. 6, 1992, abandoned.

[51] Int. Cl.$^6$ ............................ C12Q 1/68; C12P 19/34
[52] U.S. Cl. ............................ 435/6; 435/91.2; 935/77; 935/78
[58] Field of Search ............................ 435/6, 91.2, 288, 435/7.1, 7.2, 7.21, 7.32; 935/77, 78

[56] References Cited

U.S. PATENT DOCUMENTS

| | | | |
|---|---|---|---|
| 4,447,546 | 5/1984 | Hirschfeld | 436/527 |
| 4,558,014 | 12/1985 | Hirschfeld et al. | 436/527 |
| 4,582,809 | 4/1986 | Block et al. | 436/527 |
| 4,608,344 | 8/1986 | Carter et al. | 436/34 |
| 4,654,532 | 3/1987 | Hirschfeld | 250/458.1 |
| 4,683,195 | 7/1987 | Mullis et al. | 435/91.2 |
| 4,716,121 | 12/1987 | Block et al. | 435/514 |
| 4,844,869 | 7/1989 | Glass | 422/68 |
| 4,909,990 | 3/1990 | Block et al. | 422/8.11 |
| 5,001,051 | 3/1991 | Miller et al. | 435/6 |
| 5,118,605 | 6/1992 | Urdea | 435/6 |
| 5,242,797 | 9/0993 | Hirschfeld | 435/6 |

FOREIGN PATENT DOCUMENTS

| | | |
|---|---|---|
| 0320308A2 | 12/1988 | European Pat. Off. |
| 0297379 | 1/1989 | European Pat. Off. |
| 0439182A2 | 1/1991 | European Pat. Off. |
| 2190189 | 3/1987 | United Kingdom |
| 2235292 | 7/1990 | United Kingdom |
| WO90/01157 | 7/1989 | WIPO |

OTHER PUBLICATIONS

Nicholls et al. (1989) Journal of Clinical Laboratory Analysis, vol. 3, pp. 122–135, "Nucleic Acid Analysis by Sandwich Hybridization".

Guatelli et al. (1990, Mar.) Proceedings of the National Academy of Sciences, vol. 87, pp. 1874–1878, "Isothermal, in vitro amplification of nucleic acids by a multienzyme rxn modeled after retroviral amplification".

Ostergaard et al. (1991) European Journal of Clinical Microbiology and Infections Diseases, vol. 10(12), 1057–1061, see abstract.

Clin Chem. 37/9, 1482–1485 (1991) *Polymerase Chain Reaction and $Q^HT$ Replicase Amplification*, Cahill.

Journal of Immunological Methods, 74 (1984) 253–265, *Immunoassays at a Quartz–Liquid Interface: Theory, Instrumentation, etc.*, Sutherland.

Analytical Chemistry, vol. 45, No. 4, Apr., 1973, *Multiple Internal Reflection Fluorescence Spectrometry*, Harrick.

Clin Chem. vol. 35, No. 9, 1989, *Chemiluminescent Substrates for Alkaline Phosphatase: Application to Ultrasensitive Enzyme–Linked Immunoassays and DNA Probes*, Schaap.

Clin Chem. vol. 35, No. 9, 1989, *Chemiluminescent Detection of Herpes Simplex Virus I DNA in Blot and In–Situ Hybridization Assays*, Bronstein et al.

Proc. Natl. Acad. Sci. USA, vol. 87, 4514–4518, Jun. 1990 *Imaging of DNA Seq. with Chemiluminescence*, Tizard et al.

Analytical Biochemistry, 180, 95–98 (1989), *A Comparison of Chem. and Colorimetric Substrates in a Hepatitis B Virus DNA Hybridization Assay*, Bronstein et al.

Journal of Immunological Methods, 8 (1975) 235–240, *A New Immunoassay Based on Fluorescence Excitation by Internal Reflection Spectroscopy*, Kronick et al.

Nucleic Acids Research, vol. 16, No. 11, 1988, *A Comparison of Non–Radioisotopic Hybridization Assay Methods Using Fluorescent, Chem. and Enzyme Labeled Synthetic Oligodeoxyribonucleotide Probes*, Urdca, et al.

Nucleic Acids Research, vol. 13, No. 7, 1985, *The Synthesis of Oligonucleotides Containing an Aliphatic Amino Group at the 5' Terminus: Synthesis of Fluorescent DNA Primers for use in DNA Sequence Analysis*, Smith.

Bio/Technology, vol. 10, Apr., 1992, *Simultaneous Amplification and Detection of Specific DNA Sequences*, Higuchi et al.

*Primary Examiner*—Lisa B. Arthur
*Attorney, Agent, or Firm*—Thomas D. Brainard; Paul D. Yasger

[57] ABSTRACT

An apparatus and method for detecting amplified target nucleic acid is provided wherein the presence and concentration of amplified target is determined by total internal reflection over the course of the amplification reaction. A method and apparatus for detecting target nucleic acid is also provided wherein the presence and concentration of target is determined by total internal reflection and coupling of the target to the TIR element by scissile linkage. An improved immunoassay using total internal reflection and differential temperature cycling is further provided.

13 Claims, 4 Drawing Sheets

METHOD FOR DETECTION OF NUCLEIC ACID USING TOTAL INTERNAL REFLECTANCE

This application is a continuation of U.S. patent application Ser. No. 08/311,389, filed Sep. 23, 1994, now abandoned which is a continuation of application Ser. No. 07/863,553, filed Apr. 6, 1992, now abandoned.

FIELD OF THE INVENTION

The present invention relates to methods, apparatus, and kits for amplifying and/or detecting target nucleic acid using total internal reflection ("TIR") techniques. The invention also relates to an improved TIR device and method for specific binding assays, including immunoassays.

BACKGROUND DESCRIPTION

The amplification of nucleic acids is useful in a variety of applications. For example, nucleic acid amplification methods have been used in the identification of genetic disorders such as sickle-cell anemia and cystic fibrosis, in detecting the presence of infectious organisms, and in typing and quantification of DNA and RNA for cloning and sequencing.

Methods of amplifying nucleic acid sequences are known in the art. One method, known as the polymerase chain reaction ("PCR"), utilizes a pair of oligonucleotide sequences called "primers" and thermal cycling techniques wherein one cycle of denaturation, annealing, and primer extension results in a doubling of the target nucleic acid of interest. PCR amplification is described further in U.S. Pat. Nos. 4,683,195 and 4,683,202, which are incorporated herein by reference.

Another method of amplifying nucleic acid sequences known in the art is the ligase chain reaction ("LCR"). Like PCR, LCR utilizes thermal cycling techniques. In LCR, however, two primary probes and two secondary probes are employed instead of the primer pairs used in PCR. By repeated cycles of hybridization and ligation, amplification of the target is achieved. The ligated amplification products are functionally equivalent to either the target nucleic acid or its complement. This technique is described more completely in EP-A-320 308 and EP-A-439 182.

Other methods of amplifying nucleic acids known in the art involve isothermal reactions, including the reaction referred to as Q-beta ("Qβ") amplification [See, for example, Kramer et al., U.S. Pat. No. 4,786,600, WO 91/04340, Cahill et al., *Clin. Chem.*, 37:1482–1485 (1991); Pritchard et al., *Ann. Biol. Clin.*, 48:492–497 (1990)]. Another isothermal reaction is described in Walker et al., "Isothermal in vitro amplification of DNA by a restriction enzyme/DNA polymerase system", *Proc. Natl. Acad. Sci.*, 89:392–396 (1992). These amplification reactions do not require thermal cycling.

Amplification of nucleic acids using such methods is usually performed in a closed reaction vessel such as a snap-top vial. After the amplification, the reaction vessel is then opened and the amplified product is transferred to a detection apparatus where standard detection methodologies are used.

In some cases, the amplified product is detected by denaturing the double-stranded amplification products, and treating those products with one or more hybridizing probes having a detectable label. The unhybridized probes are typically separated from the hybridized probe, requiring an extra separation step. Alternatively, the primer or probes may be labeled with a hapten as a reporter group. Following amplification, the hapten, which has been incorporated into the amplification product, can be used for separation and/or detection.

In yet another detection method, the amplification products may be detected by gels stained with ethidium bromide. In sum, $^{32}P$ tracings, enzyme immunoassay [Keller et al., *J. Clin. Microbiology*, 28:1411–6 (1990)], fluorescence [Urdea et al., *Nucleic Acids Research*, 16:4937–56 (1988); Smith et al., *Nucleic Acids Research*, 13:2399–412 (1985)], and chemiluminescence assays and the like can be performed to detect nucleic acids in a heterogeneous manner [Bornstein and Voyta, *Clin. Chem.*, 35:1856–57 (1989); Bornstein et al., *Anal. Biochem.*, 180:95–98 (1989); Tizard et al., *Proc. Natl. Acad. Sci.*, 78:4515–18 (1990)] or homogeneous manner [Arnold et al., U.S. Pat. No. 4,950,613; Arnold et al., *Clin. Chem.*, 35:1588–1589 (1989); Nelson and Kacian, *Clinica Chimica Acta*, 194:73–90 (1990)].

In each case, however, these detection procedures have serious disadvantages. First, when the reaction vessel containing a relatively high concentration of the amplified product is opened, a splash or aerosol is usually formed. Such a splash or aerosol can be sources of potential contamination, and contamination of negative, or not-yet amplified, nucleic acids is a serious problem and may lead to erroneous results.

Similar problems concerning contamination may involve the work areas and equipment used for sample preparation, preparation of the reaction reagents, amplification, and analysis of the reaction products. Such contamination may also occur through contact transfer (carryover), or by aerosol generation.

Furthermore, these previously described detection procedures are time-consuming and labor intensive. In the case of both hybridization probes and hapten detection, the amplification reaction vessel must be opened and the contents transferred to another vessel, medium or instrument. Such an "open" detection system is disadvantageous as it leads to further contamination problems, both airborne and carryover.

Thus, a need emerges for detecting amplified nucleic acids in a closed system in order to eliminate the potential for contamination. Also, a need emerges for a method of amplifying and detecting the target nucleic acid in an operationally simple, yet highly sensitive manner. The ability to detect the amplification product in a sealed vessel, or in a closed system, offers useful advantages over existing prior art methods, including the ability to monitor the amplification of target nucleic acid throughout the course of the reaction.

The use of total internal reflection fluorescence techniques is known in the art with respect to immunoassays [Harrick, et al., *Anal. Chem.*, 45:687 (1973)]. Devices and methods that use total internal reflection fluorescence for immunoassays have been described in the art by Hirschfield, U.S. Pat. Nos. 4,447,564, 4,577,109, and 4,654,532; Hirschfield and Block, U.S. Pat. Nos. 4,716,121 and 4,582,809, which are all incorporated herein by reference. Other descriptions and uses are given by Glass, U.S. Pat. No. 4,844,869; Andarde, U.S. Pat. No. 4,368,047; Hirschfield, GB 2,190,189A; Lackie, WO 90/067,229; Block, GB 2,235,292A, and Carter et al., U.S. Pat. No. 4,608,344.

Use of total internal reflection elements allows performing a homogeneous assay (i.e. free of separation and wash steps) for members of specific binding pairs. Several applications of this principle are known in the art [such as Kronick, et al. *J. Immunol. Methods*, 8:235 (1975) and U.S. Pat. No. 3,604,927] for hapten assays and for immunoassay of macromolecules [Sutherland et al., *J. Immunol. Methods*, 74:253 (1984)].

In known total internal reflectance methods, however, the slow diffusion of members of specific binding pairs from the bulk of the solution to the surface of the TIR element creates a limitation in using TIR fluorescence techniques. Thus, prior art devices have used capillary tubes or flow cells to enhance diffusion either by limiting the diffusion distances or by continuous exposure to fresh reactant stream, or both. But these systems, too, have drawbacks that make them less than optimal for clinical biological applications. Capillary tubes are difficult to manipulate and are not easily automated. Flow cells require extensive washing in an effort to reduce carryover contamination before they can be reused.

Thus, in addition to a need for contamination-free, closed amplification systems, there is also a need in the art for better TIR assay systems that are more easily automated and even disposable if desired.

SUMMARY OF THE INVENTION

Several objectives and advantages of the present invention may be stated. First, the invention can monitor the presence and/or concentration of target molecules in real time. This is particularly of interest in nucleic acid amplification reactions. In addition, it is an object of the present invention to reduce contamination of other samples and other unused vessels and reagents with the amplified target nucleic acid through the use of a sealed vessel in which both amplification and detection occur. A still further object of the present invention is to provide relatively simple and sensitive methods and apparatus for detecting target nucleic acid or other molecules of interest in a reaction sample.

Accordingly, in a first aspect, the invention is a method of detecting amplified target nucleic acid using total internal reflection, comprising the steps of:

providing a reaction vessel having disposed therein (a) a reaction sample, (b) a total internal reflection (TIR) element, (c) a plurality of members of initiator sequence sets and reagents for producing amplification of target nucleic acid present in the reaction sample, (d) label means which is coupled to a fluorophore, and (e) capture means for bringing said fluorophore within the penetration depth of said element, wherein at least one of said label means and said capture means is specific for said target nucleic acid;

producing an evanescent electromagnetic wave in the TIR element which penetrates into the reaction sample adjacent the element and has an associated penetration depth;

reacting the reaction sample, the initiator sequences and amplification reagents under conditions sufficient to amplify target nucleic acid present in the reaction sample to produce amplification products;

capturing said label means within the penetration depth as a function of the presence or amount of target nucleic acid; and detecting within the TIR element a change in fluorescence.

The invention contemplates both covalent attachment and specific binding member attachment of initiators to the element to bring the fluorophore within the penetration depth. Both immunoreactive and polynucleotide specific binding pairs are contemplated. It is preferred that the amplification initiators double as either capture means or label means or both.

The invention also provides an apparatus for amplification and detection of nucleic acid targets comprising:

a sealed, static-volumetric reaction vessel adapted to contain a reaction sample and reagents for amplification a total internal reflection (TIR) element disposed in said reaction vessel such that substantial surface area of the element is in contact with said reaction sample and such that one end of the element protrudes from the vessel;

means for producing an evanescent electromagnetic wave in the TIR element which penetrates into the reaction sample adjacent the element and has an associated penetration depth;

temperature control means for reacting the reaction sample and amplification reagents under cyclic temperature conditions sufficient to amplify target nucleic acid present in the reaction sample and to capture a fluorophore capable of emitting fluorescence within the penetration depth of the element as a function of the presence or amount of target in the sample; and means for detecting in the TIR element a change in fluorescence.

Preferably the reaction vessel and the TIR element are separated from one another by a distance that precludes capillary migration. For wettable vessels and aqueous solutions a distance of 1.7 mm or more is sufficient. The reaction vessel may be sealed by a sealing member having a throughbore for the TIR element, or by an integral cap/TIR element.

In another aspect, the invention relates to a method and apparatus for detecting nucleic acid in a sample by means of signal amplification achieved by destroying, as a function of the amount of target present, a scissile link that holds fluorophore near the TIR element. Thus, a decrease in the totally internally reflected fluorescence will occur in the presence of target.

In a final aspect, the invention relates to an improved method and apparatus for conducting specific binding assays with fluorophore labels that are detected or monitored by total internal reflectance means. This embodiment of the invention includes:

a sealed, static-volumetric reaction vessel adapted to contain a reaction sample and reagents for a specific binding assay; and a total internal reflection (TIR) element disposed in said reaction vessel such that substantial surface area of the element is in contact with said reaction sample and such that one end of the element protrudes from the vessel;

wherein said static-volumetric reaction vessel and TIR element are dimensioned such that the space between the element surface and the interior wall of the reaction vessel is too great to support capillary migration of an aqueous fluid.

The invention also provides kits for detecting amplified nucleic acids, comprising PCR or LCR amplification reagents and a TIR element having a plurality of coupling sites that allow attachment of amplified target nucleic acid.

DETAILED DESCRIPTION

A. TIR Principles

Figure 1:
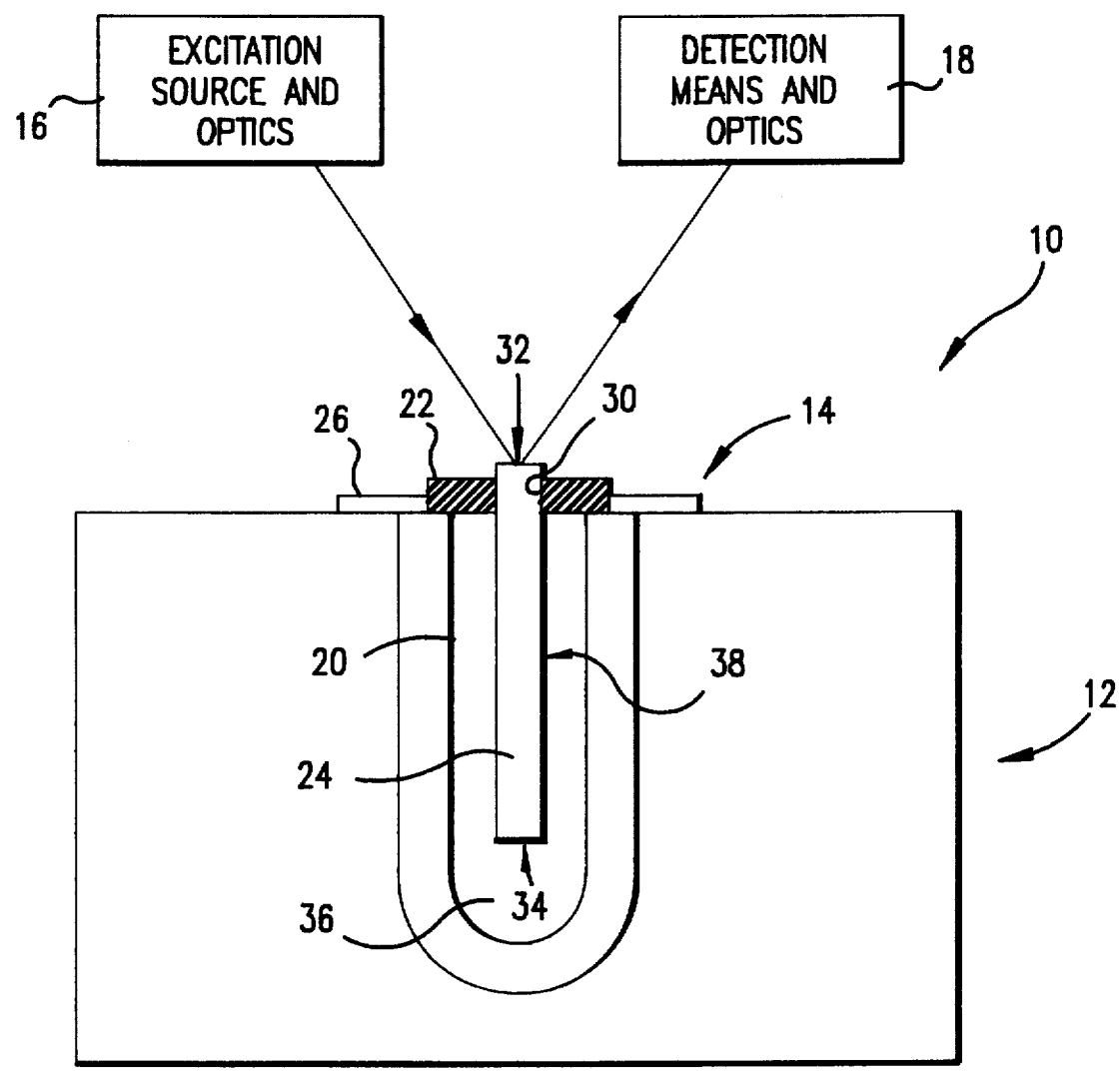
FIG. 1 is a schematic illustration of a detection system in accordance with one embodiment of the present invention.

Total internal reflection ("TIR") is known in the art and operates upon the principle that light striking the interface between two media having different refractive indices ($N_1 > N_2$) from the denser medium (i.e. having the higher refractive index; here $N_1$) can be made to totally internally reflect within the medium if it strikes the interface at an angle, $\theta_R$, greater than the critical angle, $\theta_C$, where the critical angle is defined by the equation:

$$\theta_C = \arcsin(N_2/N_1)$$

Under these conditions, an electromagnetic waveform known as an evanescent wave is generated in the less dense medium, and the electric field associated with the excitation light forms a standing sinusoidal wave, normal to the interface, is established in the denser medium. The evanescent wave penetrates into the less dense medium, but its energy dissipates exponentially as a function of distance from the interface. A parameter known as "penetration depth" ($d_p$) is defined as the distance from the interface at which the evanescent wave energy has fallen to 0.368 times the energy value at the interface. [See, Sutherland et al., *J. Immunol. Meth.*, 74:253–265 (1984)]. Penetration depth is calculated as follows:

$$d_p = \frac{\lambda/N_1}{2\pi\{\sin^2\theta_R - (N_2/N_1)^2\}^{1/2}}$$

Factors that tend to increase the penetration depth are: increasing angle of incidence, $\theta_R$; closely matching indices of refraction of the two media (i.e. $N_2/N_1 \to 1$); and increasing wavelength, $\lambda$. An example will illustrate. If a quartz TIR element ($N_1=1.46$) is placed in a aqueous medium ($N_2=1.34$), the critical angle, $\theta_C$, is 66°. If 500 nm light impacts the interface at $\theta_R=70°$ (i.e. greater than the critical angle) the $d_p$ is approximately 150 nm.

For cylindrical and fiber optic TIR elements, the maximum acceptance angle with regard to the TIR element axis, B, for the radiation entering the TIR element and so propagated within it, is established by the refractive indices of the TIR element and the surrounding medium. For radiation initially propagating through a medium of refractive index $N_O$, such as air, incident upon a TIR element of refractive index $N_1$, otherwise surrounded by a medium of refractive index $N_2$, the maximum acceptance angle, B, may be found from the equation:

$$N.A. = N_O \sin B = (N_1^2 - N_2^2)^{1/2},$$

where N.A. is the so-called numerical aperture of the TIR element.

Within the penetration depth, the evanescent wave in the less dense medium (typically a reaction solution) can excite fluorescence in the sample. The fluorescence tunnels back into the TIR element propagates within the TIR element along the same path as the standing sinusoidal wave (but at a different wavelength) and is detected. All of the radiation that tunnels back into the TIR element is within the total internal reflection angle and is thus trapped within the TIR element. Accordingly, TIR allows detection of a fluorophore-labeled target of interest as a function of the amount of the target in the reaction sample that is within the penetration depth of the TIR element.

B. A First Embodiment

In accordance with a first embodiment of the present invention, total internal reflection is used to detect amplified target nucleic acid in a reaction vessel. The reaction vessel preferably is sealed although a flow cell or a capillary tube may be used. Both amplification and detection can take place within the same closed reaction vessel, thus minimizing contamination risks.

FIG. 1 illustrates a an amplification and detection system 10 in accordance with one embodiment of the present invention. The system includes a thermal cycling device generally represented as 12, a reaction unit generally represented as 14, fluorescence excitation source and optics 16 and fluorescence detection optics 18. The unit 14 includes a reaction vessel 20, a sealing member 22 and a total internal reflection (TIR) element 24. The reaction vessel 20 is placed in a thermal cycling device 12 and is supported by tab members 26.

Amplification reactions using thermal cycling are presently preferred over isothermal mechanisms. It is believed that convection currents resulting from the successive heating and cooling cycles during thermal cycling enhances diffusion of molecules in the reaction sample, although (in contrast to an embodiment described later) this feature is not deemed essential to this embodiment. Accordingly, a thermocycler device 12 is shown. However, the details of the method of thermocycling are not critical to the invention. For example, the temperature of the amplification reaction may be controlled manually, such as by air or water baths, or regulated automatically by a thermocycler device specifically designed for nucleic acid amplification. Thermocycler devices are commercially available from Perkin-Elmer Corporation, (Norwalk, Conn.) and Coy Laboratories, (Ann Arbor, Mich.).

The reaction vessel 20 is made of glass or polymeric materials such as polystyrene, polyacrylate and the like, and is preferably made of a thermostable material. Preferably, the size of the reaction vessel 20 is selected so as to contain relatively small quantities of reaction sample. More preferably, the reaction vessel 20 is selected to so as to contain from about 50 ul to about 200 ul reaction sample. In a typical embodiment, the reaction vessel 20 is a microcentrifuge tube, although other configurations are possible and within the invention. As will be described (and defined) in more detail below in connection with another embodiment, it is preferred that the reaction vessel be a "static-volumetric" vessel, having a composition (with regard to wettability) and a distance between the element surface 38 and the walls of the reaction vessel 20 that is sufficiently great to prohibit capillary action of an aqueous sample therebetween.

The TIR element 24 may be preferably any of a number of optically transparent materials, including but not limited to, glass, quartz, and transparent polymers such as polystyrene or polystyrene copolymers and polyacrylic acids or the like, chosen to have an index of refraction greater than that of the medium in which it is placed. Preferably the medium is an aqueous reaction sample comprising amplification reaction reagents and target nucleic acids. Such a reaction medium typically will have a refractive index ranging from about 1.30 to about 1.38, more typically, about 1.34. Thus, for a visible light beam having a wavelength ranging frown about 480 to 540 nm, the preferred TIR elements according to the invention have refractive indices ranging from about 1.4 to 1.6. Exemplary materials and their approximate refractive indices are given in Table 1 below:

TABLE 1

| Element Material | Refractive Index |
| --- | --- |
| Quartz | 1.6 |
| Polystyrene | 1.59 |
| Glass | 1.52 |
| Polymethylmethacrylate | 1.49 |
| Pyrex | 1.47 |

The TIR element 24 is further chosen to be insoluble and non-reactive with the reaction sample. An exemplary TIR element 24 is a glass rod with a wide surface area and a diameter of approximately 1 millimeter. It will be understood that the dimensions of the TIR element 24 accommodate the reaction being undertaken and the size of the reaction vessel 20. Those skilled in the art will appreciate that the surface area of the TIR element 24 should be considered and it is believed that to obtain maximum surface area binding, the reaction vessel 20 and the TIR element 24 are preferably long and cylindrical.

As shown in FIG. 1, a sealing member 22 is configured and dimensioned to fit on the open end of the reaction vessel 20. A centrally disposed bore 30 in the sealing member 22 is adapted to support an upper end portion of the TIR element 24 substantially coaxially within the vessel 20. Additionally, the sealing member 22 preferably provides a sturdy locating surface (e.g. tab members 26) for positioning the unit 14 with respect to the excitation source and optics 16 and detection optics 18, which will be described in more detail in connection with FIG. 2. The sealing member 22 is preferably a rubber septum or a polymer or polymer laminate.

The TIR element 24 passes through and is supported by the sealing member 22 so as to expose as much as possible of the TIR element 24 to the interior of the reaction vessel 20, leaving only an end face 32 unobscured and approximately coterminous with the extremity of the bore 30 external to the vessel 20. The end face 32 of the TIR element 24, however, does not have to be coterminous with the extremity of the bore 30 as can be seen from alternative TIR elements shown in FIGS. 3 and 4. It is important, however, that a minimum amount of the TIR element is exposed above the sealing member 22 to reduce the dissipation of signals received and transmitted by the TIR element 24. Preferably the end face 32 is highly transparent and free of blemishes which would tend to scatter light incident upon its face. The end face 32 may be optically polished, or alternatively, a fused quartz TIR clement 24 may be cleaved to provide an adequate optical surface. Other TIR element configurations will be described with reference to FIGS. 3 and 4.

Alternatively, the TIR element may be fabricated by injection molding of chemically activated transparent polymers into an appropriate shape and finish. Chemically-activated transparent polymers include surface treated homopolymers (e.g. polystyrene), and copolymers of styrene such as styrene maleic anhydride (commercially available from ARCO Chemical Company). It is very likely that other polymers and copolymers are suitable provided they are transparent and chemically activatable.

In the embodiment of FIG. 1, opposite end face 34 of the TIR element 24 is also polished flat or cleaved and, preferably, is further provided with a black coating, a mirror coating or a separate mirror disposed substantially normal to the TIR element 24 axis. It is important in the operation of the invention to avoid fluorescent excitation of the bulk reaction solution by light exiting the TIR element 24 through the end face 34. Thus, a black coating (to absorb) or a mirror coating (to reflect) are preferred. The mirror coating or separate mirror has the added advantage of causing radiation trapped in the TIR element 24 to double pass the TIR element 24. The end face 34 need not be flat or normal to the axis of the element, however, as shown from FIG. 3.

In the interior of the reaction vessel 20, the TIR element 24 is exposed to the reaction sample 36. The reaction sample 36 typically includes a buffered solution of sample components, label means and reagents for amplification (described further below). Examples of typical reaction samples for particular amplification reactions are provided in Examples 4–11 below.

The outer surface 38 of the TIR element 24 is modified, as described further below, having a plurality of coupling sites that allow attachment of the amplification reaction products or other members of specific binding pairs that can capture amplification reaction products. The amplified product, typically a double-stranded nucleic acid, comprises a pendent fluorophore, as described more fully below. During the course of or after the amplification reaction, the amplified product and associated fluorophore is brought within the penetration depth of the TIR element 24 so that a fluorescent signal may be detected.

C. Reagents and Protocols

The target nucleic acid of the present invention is that nucleic acid sequence sought to be detected. It may comprise deoxyribonucleic acid (DNA) or ribonucleic acid (RNA), or may be natural or synthetic analogs, fragments, and/or derivatives thereof. The target is preferably a naturally-occurring nucleic acid of prokaryotic or eukaryotic origin, including but not limited to, human, human immunodeficiency virus (HIV), human papilloma virus (HPV), herpes simplex virus (HSV), Chlamydia, Mycobacterium, Streptococcus, and Neisseria. One of skill in the art will recognize that thousands of other target nucleic acid sources are possible. When possible, DNA is often preferred due to its better stability.

As mentioned above, the outer surface 38 of the TIR element 24 is modified to include a plurality of coupling sites for attachment of "capture means" for bringing fluorophore within the penetration depth. Various capture means are described below, and include covalent bonding mid specific binding pair attachment. In addition to the "capture means", it is necessary to have a "label means" for absorbing and re-emitting the fluorescent energy. The label means comprises a fluorophore, which is capable of absorbing fluorescent energy at one wavelength and re-emitting energy at a different wavelength, as is known in the art. Either the capture means or the label means, or both, must be specifically associated with the presence or amount of target. The present TIR invention depends on the ability to bring the label means within the penetration depth in amounts that correspond to the presence or amount of the target.

A third reagent system is necessary for amplification of the target. Amplification reactions contemplated by the present invention include, but are not limited to, thermal cycling reactions such as PCR and LCR, and isothermal reactions such as Q-beta and restriction/polymerase amplification. Other amplification systems yet to be developed may also be useful. Target amplification typically requires a polynucleotide complementary to a region of the target molecule. The term "initiator", as used in the present invention, is intended to refer generally to such a polynucleotide which is capable of sufficiently hybridizing with the target nucleic acid to commence the amplification process. Initiators are selected to be complementary to various portions of the target nucleic acid. For purposes of this invention, no distinction is drawn between "polynucleotide" and "oligonucleotide".

primer labeled with a hapten at its 5' end might fulfill the function of initiator while the hapten serves as a capture means. In such a case, the primer is referred to as a "capture initiator". Similarly, an LCR probe labeled with a fluorophore might fulfill the function of initiator and label means, and is thereby called a "label initiator". Table 2, below, provides several possible configurations and reaction protocols, all of which are within the present invention.

TABLE 2

Figure 5A:
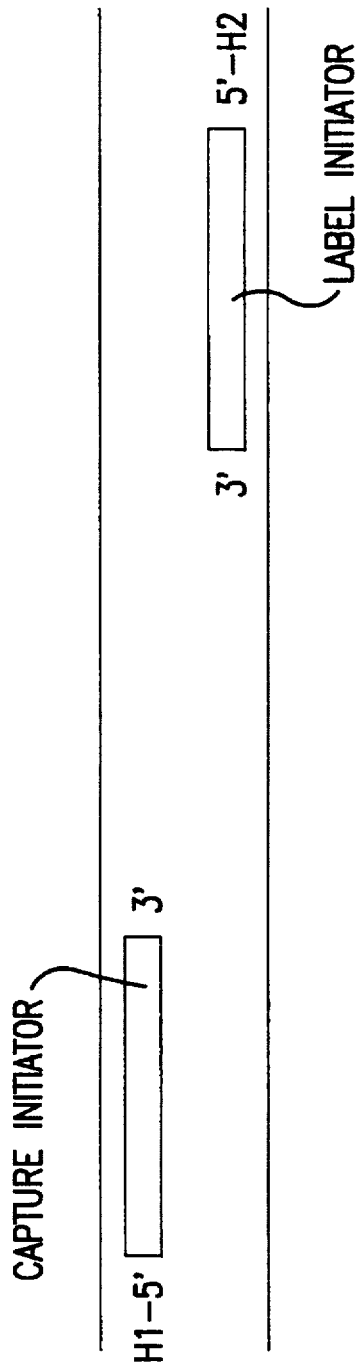
FIG. 5A illustrates a preferred configuration for PCR amplification, using a capture initiator and a label initiator.
Figure 5B:
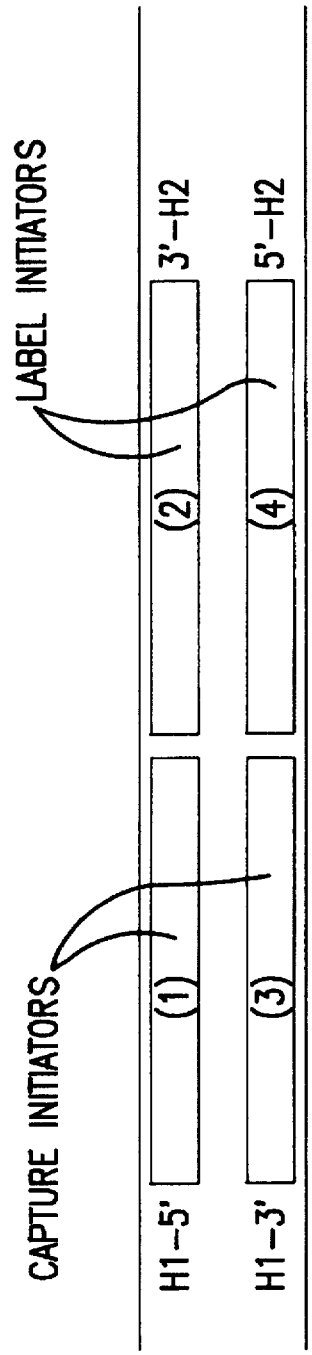
FIG. 5B illustrates a preferred configuration for LCR amplification, using capture initiator and label initiator probe pairs.

| Reaction Type | Initiator (refer to FIGS. 5A and 5B for orientation) | Capture Means | Label Means |
|---|---|---|---|
| Solution phase PCR | unmodified primers | 1) Specific capture probe | a) Specific label probe; or b) Incorporation of dNTPs labelled with fluorophore |
| | one primer only modified with a specific binding member such as a hapten or polynucleotide tail | Capture initiator: (with anti-hapten or complementary polynucleotide on element) | a) Specific label probe; or b) Incorporation of dNTPs labelled with fluorophore |
| | one primer only modified with a specific binding member such as a hapten, polynucleotide tail, or fluorophore | 1) Specific capture probe | Label initiator: (with anti-hapten or complementary polynucleotide conjugate with fluorophore, if not directly labeled with fluorophore) |
| | both primers labeled (one with a specific binding member; other with a different specific binding member or fluorophore | Capture initiator: (with anti-hapten or complementary polynucleotide on element) | Label initiator: (as above) |
| Solid phase PCR | primer is covalently bound to element surface (optionally via a chemical or polynucleotide spacer) | bound primer is Capture initiator | a) Specific label probe; or b) Incorporation of dNTPs labelled with fluorophore; or c) Label initiator: (as above) |
| Solution phase LCR | unmodified probes | 1) Specific capture probe | a) Specific label probe; or b) Incorporation of dNTPs labelled with fluorophore using gap fill LCR |
| | left one or two probes modified with a specific binding member such as a hapten or polynucleotide tail | Capture initiator: (with anti-hapten or complementary polynucleotide on element) | a) Specific label probe; or b) Incorporation of dNTPs labelled with fluorophore using gap fill LCR |
| | right one or two probes modified with a specific binding member such as a hapten, polynucleotide tail, or fluorophore | 1) Specific capture probe | Label initiator: (with anti-hapten or complementary polynucleotide conjugate with fluorophore, if not directly labeled with fluorophore) |
| | both right and left probes labeled (right with a specific binding member; left with a different specific binding member or fluorophore | Capture initiator: (with anti-hapten or complementary polynucleotide on element) | Label initiator: (as above) |
| Solid phase LCR | at least one of left probes is covalently bound to element surface (optionally via a chemical or polynucleotide spacer) | bound probe(s) is (are) Capture initiator | a) Specific label probe; or b) Incorporation of dNTPs labelled with fluorophore; or c) Label initiator: (as above) |

The initiator serves different functions depending upon the type of amplification reaction employed. In the PCR amplification reaction, the initiator (typically referred to in the art as a primer) acts as a point of hybridization and initiation of the enzymatic polymerization step that results in extension. Each initiator is then extended by a polymerase using the target nucleic acid as a template. The extension products become target sequences themselves, following dissociation from the original target strand. For LCR amplification, the initiators, (typically referred to in the art as probes) comprise four polynucleotides, two of which (primary) hybridize to the target strand such that they become ligated together, and two of which (secondary) hybridize to the target complement or the ligated primary product and are similarly ligated. Both PCR and LCR are amply described in the art and need not be detailed here.

It will be realized that by modifying the initiators, it is possible for the functions of capture and/or label to be accomplished by the initiators themselves, alone or in combination with accessory reagents. For example, a PCR In a particularly preferred embodiment, the initiators serve all three functions (initiation of amplification, capture means and label means). Capture and label initiators for PCR are illustrated generally in FIG. 5A. At the end of several cycles in the presence of target (to serve as template for initial extension), the predominant product is a bihaptenated duplex. Other examples of capture and label initiators that may be utilized for PCR amplification reactions in the present invention are provided in Table 3 of Example 1 below. Analogously, capture and label initiator pairs for LCR are illustrated generally in FIG. 5B, although they need not be blunt ended as shown. Arbitrarily, initiator (1) and initiator (3) (referred to in Table 2 as "left probes") are designated capture initiator sequences and initiators (2) and (4) (referred to in Table 2 as "right probes") are designated label initiator sequences. Once the initiators (1) and (2) are ligated, (an event that is essentially dependent on the presence of target) the fused product is bihaptenated, bearing a first hapten (H1) on one end and a second hapten (H2) on the other. One hapten is used for capture and the other is used for labeling. Initiators (2) and (4) might also have been labelled directly with a fluorophore. Other examples of capture and label initiators that may be utilized for LCR in the present invention are provided in Table 3 of Example 1 below.

Preferably, the initiator is synthesized using nucleotide phosphoramidite or phosphonate chemistry techniques known in the art and/or instruments commercially available from Applied Biosystems, Inc. (Foster City, Calif.), DuPont (Wilmington, Del.) or Milligen (Bedford, Mass.). Initiator synthesis using such techniques is described further in Example 1 below. Alternatively, the initiator may be obtained by digesting naturally-occurring nucleic acids and isolating fragments of interest.

Many different haptens are known, and virtually any hapten may be used with the present invention. Many methods of adding haptens to probes are known in the literature. Enzo Biochemical (New York) and Clontech (Palo Alto) both have described and commercialized probe labelling techniques. For example, a primary amine can be attached to a 3' oligo end using 3'-Amine-ON CPG™ (Clontech, Palo Alto, Calif.). Similarly, a primary amine can be attached to a 5' oligo end using Aminomodifier II® (Clontech). The amines can be reacted to various haptens using conventional activation and linking chemistries. Alternatively, certain haptens and labels are commercially available as phosphoramidite reagents and can be incorporated directly into initiators during synthesis.

In addition, copending applications U.S. Ser. Nos. 625,566, filed Dec. 11, 1990 abandoned Sep. 7, 1993 and Ser. No. 630,908, filed Dec. 20, 1990 which issued as U.S. Pat. No. 5,290,925 teach methods for labelling probes at their 5' and 3' ends respectively. Both the aforementioned copending applications are incorporated by reference. Some illustrative haptens include many drugs (eg. digoxin, theophylline, phencyclidine (PCP), salicylate, etc.), T3, biotin, fluorescein (FITC), dansyl, 2,4-dinitrophenol (DNP); and modified nucleotides such as bromouracil and bases modified by incorporation of a N-acetyl-7-iodo-2-fluorenylamino (AIF) group; as well as many others. Certain haptens described herein are disclosed in U.S. Pat. No. 5,424,414 and U.S. Pat. No. 5,464,746, both filed Mar. 27, 1992 (collectively referred to herein as the "hapten applications"). The entire disclosure of each of the above hapten applications is incorporated herein by reference.

It will be apparent to those persons skilled in the art that, when initiators are labeled on the exterior ends, the length of the amplification products, including any spacers or specific binding partners, should not exceed the penetration depth. Otherwise, the fluorophore label will not become excited. Relatively short amplified targets are produced in LCR so that, even when end-labeled, exceeding the penetration depth is usually not a factor. For example, two 25-mer initiators ligated together and forming an alpha helix duplex will have a length of about 17 nm. Even with allowances for spacers and conjugation partners, this is well within the typical 150 nm penetration depth (see above). In contrast, PCR typically amplifies longer target nucleic acid sequences to generate amplification products having from about 100 to several thousand or more nucleotides, including sequences not complementary to the initiator. Thus, for PCR it is preferable to select primers that are relatively close together, or to label the amplification product at internal positions, away from the extreme ends.

The length of the initiator sequence will also depend on various factors, including but not limited to, amplification reaction temperature, source of the initiator sequence, complexity of the target sequence, and the method of amplification. Preferably, the initiator sequence is sufficiently long to provide desired specificity in order to avoid hybridization with random sequences that may be present in the reaction sample. However, particularly with PCR the specificity can be improved using a specific capture or label probe internal to the primers. Preferably, the initiator sequence comprises from about 15 to about 100 bases, and more preferably, from about 15 to about 40 bases.

The amount of initiator added to the reaction sample or, in the case of bound capture initiators, coupled to the TIR element, may be determined empirically by those persons skilled in the art. Generally, the amount of initiator added will be similar to that typically used in nucleic acid amplification reactions, i.e. a molar excess of about $10^8$ to $10^{12}$ over the anticipated amount of target nucleic acid in the reaction sample (which inevitably is unknown in the first place). When covalently attaching bound capture initiators or bound components of capture means (e.g. anti-hapten or complementary polynucleotide) it will generally be desired to saturate the element as completely as possible.

The TIR element 24 may be modified by various means so as to allow attachment of the amplification products or other members of specific binding pairs that can capture the amplification products. It will be apparent to those persons skilled in the art that means for attaching the amplification reaction products to the TIR element should be selected in view of the amplification reaction conditions. For instance, for an amplification reaction that utilizes thermal cycling, thermostable coupling mechanisms such as covalent linkages or polynucleotide linkages should be selected, while thermolabile linkages such as antibody-hapten should be avoided. Such considerations are less critical for isothermal processes. The TIR element 24 modifications described below are provided by way of example, and are not intended to be limiting.

At least pan of the capture means is generally coupled to the TIR element 24 by covalent bonding, although antibodies may be adsorbed onto the element surface. Methods of covalently bonding antibody to glass through silyl coupling are known in the art and are described further by Weetall, U.S. Pat. No. 3,652,761. Methods of adsorbing or covalently binding antibody to polymers and chemically-activated polymers are also known in the art.

Similarly, methods of covalently bonding polynucleotides to the element are also known in the art. More particularly, a capture polynucleotide (whether initiator or specific binding partner) may be coupled to quartz or glass TIR elements using, for example, methods described in WO 89/10977 and/or WO 90/03382. Chemical binding of nucleotide base pairs to a glass surface typically involves reacting the hydroxyl moieties of the quartz or glass surface with trimethyl siloxane, substituted with a chain of methylene groups and terminating with a reactive organic functional group. Prior art silation reactions for derivatizing a glass surface are further described in GB 2,190,189A. Chemical reagents may also be reacted with a diisothiocyanate to produce amino, benzyl chloridem or isothiocyanate terminal groups on the derivatized glass surface 38 of TIR element 24. These reactive groups may then attach the capture polynucleotide (initiator or specific binding member) to the TIR element 24. Reagents for chemical binding of nucleotides to the TIR surface are commercially available from companies such as Hals America, Inc. (Piscataway, N.J.), PCR Inc., (Gainesville, Fla.) or Petrarch Chemical Co., among others.

Polynucleotides may also be coupled to chemically-activated polymeric TIR elements. For instance, styrene maleic anhydride (available from ARCO Chemical Company) comprises functional groups that allow coupling of the capture means to the TIR element. Attachment of initiators to such chemically-activated TIR elements is further described in Example 2 below. Other methods of attaching polynucleotides to polystyrene are described in Rasmussen, et al., *Anal. Biochem.*, 198:138–142 (1991).

Alternatively, capture means (whether initiator or specific binding member) may be coupled to the TIR element 24 via spacer arm linkers. As used in the present invention, the term "spacer" or "spacer arm linker" refers to a molecule that extends the capture means, and thus the captured, amplified target away from the surface of the TIR element, and that does not absorb fluorescence. One form of a "spacer" is specific binding member, such as an antibody or polynucleotide, used to capture the amplification product. Examples of specific binding member pairs include, but are not limited to, antibiotin antibodies, avidin, carbohydrates and lectin, polynucleotides. Another form of "spacer" is a chemical linker such as a heterobifunctional linker, or poly(same nucleotide) tail. In general, polynucleotides are preferred spacers since they are thermostable and encounter less steric constraints and competition for the binding sites. For instance, poly T spacer arms may be used to attach initiator sequences to TIR elements, as described further in Examples 5, 7, 9, and 11 below. Specific binding pairs, including antibodies, may also be coupled to the TIR element using prior art spacer arm chemistry.

Label means preferably comprise a detectable fluorescent label attached to at least one nucleotide or a specific binding partner. Label means are typically added to the reaction solution. It will be recalled that in some cases, it is desired to have an initiator that serves part of the label means function. To make a "direct" label initiator, a fluorophore is covalently coupled to the label initiator sequence using standard chemistry techniques known in the art [See, e.g., Goodchild, *Bioconjugate Chemistry*, 1:165–186 (1990); or Urdea, et al., *Nucl. Acids Res.*, 16:4937–4956 (1988)]. Alternatively, an "indirect" label initiator" can be prepared by haptenating one or more initiators with a hapten that is differentiable from any capture hapten that might be used.

In yet another alternative, fluorophore-labeled nucleoside triphosphates, dATP, dCTP, dTTP, dGTP (commercially available from e.g. Pharmacia-LKB Nuclear, Inc, Gaithersburg, Md.) may be incorporated into the label initiator during synthesis of the sequence. This method is particularly useful for PCR and gap filling LCR. Fluorophores contemplated by the present invention include, but are not limited to, fluorescein, rhodamine, acridine orange, and Texas red. Such fluorophores are commercially available from Sigma Chemical Company (St. Louis, Mo.), Aldrich Chemical Company (Milwaukee, Wis.), and Molecular Probes (Junction City, Oreg.). Intercalating fluorophores may also be useful in the present invention.

The present invention contemplates that single or multiple fluorophores may be coupled to a label means (whether initiator or label conjugate). It is believed that it may be advantageous to couple multiple fluorophores to the label initiator in order to enhance the fluorescent signal, particularly when the reaction sample is turbid. If multiple fluorophores are coupled to the label initiator, the fluorophores should not interfere with hybridization, polymerization or ligation. To detect multiple target nucleic acid sequences, or to detect a single target along with a control nucleic acid sequence, two different fluorophores specific to each target may be coupled to respective label initiator sequences.

Using standard chemistry techniques known in the art, it is possible to couple a fluorophore (or other label means) to the 3' or the 5' terminus of a label initiator. In PCR amplification, it is preferable to label a label initiator at the 5' hydroxyl group, since the 3' terminus is needed for extension during amplification. (See FIG. 5A). In LCR, it is preferable to couple the label means to the distal (from the element) 5' and 3' termini of the label initiators. (See FIG. 5B). The label means may also be coupled to the label initiator internally, as long as the internal coupling does not interfere with hybridization or ligation.

The fluorophore may be coupled to the label initiator directly through sites present in the sequence, such as amino groups on the bases, hydroxyl groups, and phosphate groups. Alternatively, the fluorophore may be coupled to the label initiator through some other reactive linker group introduced for that purpose. Common reactive linker groups include primary amines, thiols, or aldehydes. Reactive linker groups may also be attached to the label initiator by a spacer arm either to facilitate coupling or to distance the label means from the initiator. For instance, a hapten may be attached to the label initiator and the fluorophore may then be coupled to the initiator via anti-hapten-fluorophore conjugate binding [See, e.g., EP-A-357 011, and EP-A-439 182].

It will be readily apparent to those persons skilled in the art that, like capture coupling, fluorophore coupling techniques should be chosen in view of the amplification reaction conditions, some methods being more preferable. For example, if PCR or LCR amplification is employed, the coupling of the fluorophore or fluorophores should involve thermostable bonds since both PCR and LCR require thermal cycling.

D. System

Figure 2:
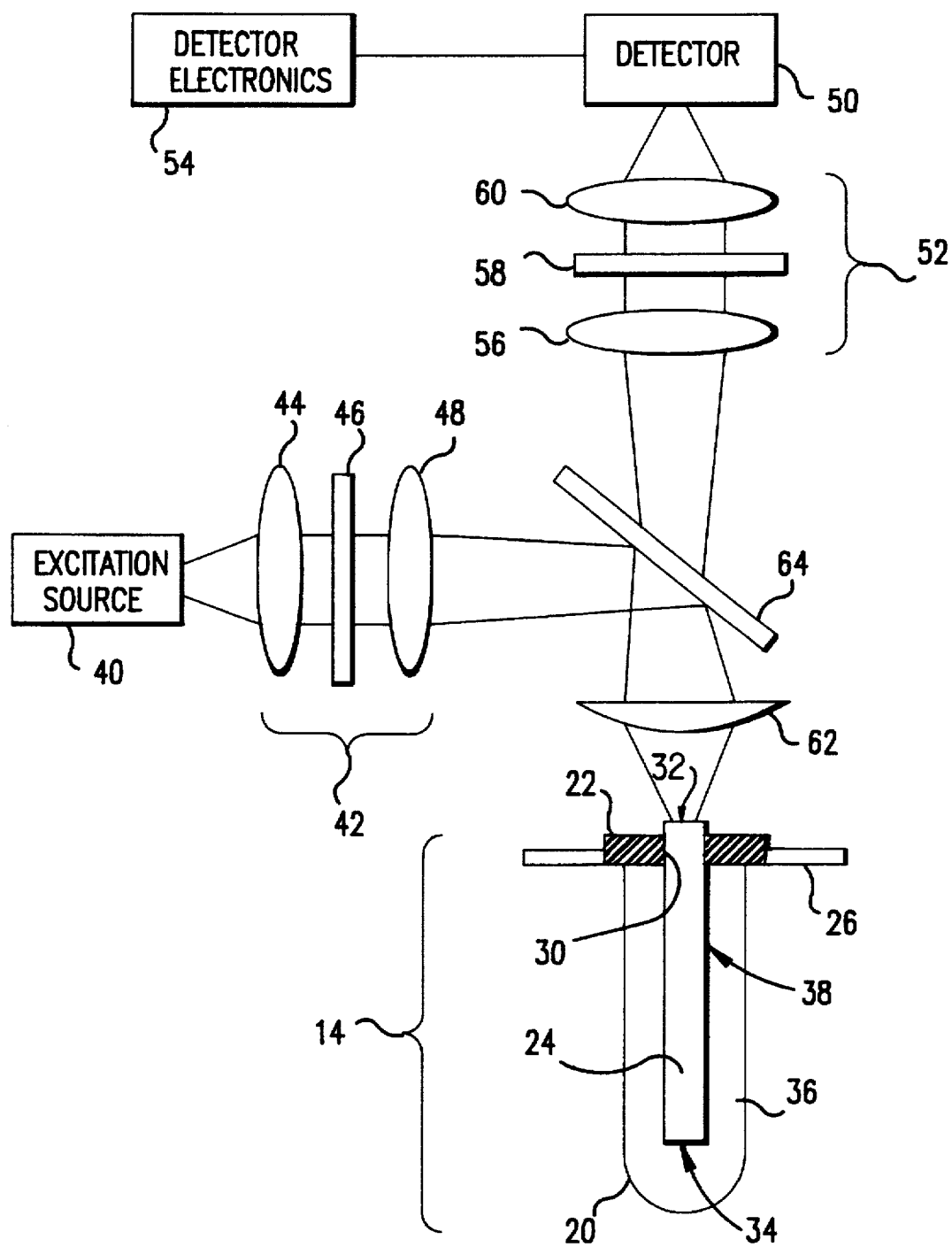
FIG. 2 illustrates the reaction vessel and associated excitation and detection optics for a detection system as shown in FIG. 1.

FIG. 2 illustrates the reaction vessel 20 and, from FIG. 1, the associated fluorescence excitation source and optics 16 and detection optics 18. The fluorescence excitation source and optics and the detection optics are conventional and well known and, in this regard, are not part of the present invention. For completeness, however, a particular configuration of the optics will be described hereinafter for exemplary purposes only. Many other configurations are possible as is well known to those skilled in the art. The excitation source and optics 16 includes a light source 40 and appropriate beam shaping optics 42, as will be well understood by those skilled in the art, to permit the source 40 to be imaged on the end face 32 of the TIR element 24. The angle of incidence of the ray on the end face 32 of the TIR 32 is within the numerical aperture of the TIR element 24 and greater than the critical angle described above. The appropriate beam shaping optics 42 may include a collimating lens 44, an excitation wavelength selection means 46 and a focusing lens 48 as is well known to those skilled in the art. The light source 40 may be a direct current-driven tungsten-halogen lamp, a phosphor-coated mercury lamp, a pulsed Xenon flash lamp or a laser. The excitation wavelength selection means 46 can be a prior art narrow band multi-cavity interference filter having a maximum wavelength transmission chosen to allow optimum excitation of the fluorophore or fluorophores selected.

The light source 40 and wavelength selection means 46 provide optical radiation of the appropriate frequency, chosen on the basis of the fluorophore or fluorophores employed, to excite fluorescence in the label means associated with amplified target nucleic acid. The light source 40 preferably provides this radiation only over a narrow wavelength band chosen to maximize fluorescence. Of course, multiple fluorophores may be used. Alternatively the light source 40 may provide optical radiation of multiple frequencies to excite multiple fluorophores. If multiple fluorophores are used, each of the fluorophores is selected so that the absorption maximum of one fluorophore is not near the emission maximum of another fluorophore, and so that the emission wavelengths are distinguishable.

The fluorescence detection optics 18 includes a detector 50, field optics 52 and detector electronics 54. The detector 50 is chosen to have maximum sensitivity in the region of peak fluorescence emission of the fluorophore; the field optics 52 restrict the detector's 50 field of view to the end face 32 of the TIR element 24, as is well known by those skilled in the art. The field optics 52 include a collimating lens 56, a fluorescence wavelength selection means 58 and a focusing lens 60. The detector 50 can be a photodiode, an avalanche photodiode, or a photomultiplier tube. When using a pulsed light source, time-gated detection can be used to improve the signal to noise characteristics of the system. The fluorescence wavelength selection filter 58 is chosen to maximize transmission of the emission fluorescence beam(s) and to have maximum blocking at other wavelengths, especially the excitation wavelength.

If multiple fluorophores are used, they may be excited at different wavelengths or each of the fluorophores may be excited at the same wavelength, but emit at different wavelengths, provided the absorption maximum of one fluorophore is not near the emission maximum of another fluorophore. If multiple fluorophores are used, detection will require multiple detectors or, alternatively, a single detector with a rotating or oscillating multiple wavelength filter. Filters situated in front of each detector are chosen to limit the radiation incident on the corresponding detector to the emission maxima of the fluorescent label while respectively blocking the fluorescence of the other material.

Interposed between the light source 40 and an objective 62 is a dichroic beam splitter 64. Preferably the dichroic beam splitter 64 is a low-pass interference filter with a cut-off frequency chosen to be between the frequencies of maximum absorption and maximum fluorescence emission of a fluorophore of interest. The dichroic beam splitter 64 thus reflects high frequency fluorescence exciting radiation from the light source 40 and transmits the low frequency radiation corresponding to the fluorescence maximum of the fluorophore. Depending upon the type of TIR element being used, a dichroic beam splitter may not be necessary. (See, e.g. FIG. 4).

The objective 62 is selected to image the light source 40 on the end face 32 of the TIR element 24 so as to fill the end face 32 with an image of the beam shaping aperture of the source 40, the maximum angle of incidence of the ray being selected to be less than that corresponding to the numerical aperture of the TIR element 24. The objective 62 is also selected so as to collect substantially all of the radiation exciting the end face 32 over the numerical aperture of the TIR clement 24 and to image the end face 32 on detector 50. As an aid in establishing the proper positioning of the TIR element 24, the excitation source and optics 16 and detection optics 18 are preferably provided with a positioning means, such as aperture plate (not shown), dimensioned to accept the bore 30 of the sealing member 22 and dimensioned to position the end face 32 appropriately relative to the objective 62.

The detection electronics 54 can be chosen from prior art direct current measurements or photon counting measurements. Those skilled in the art can make any combination of excitation and detection elements to achieve optimum detection without deviating or departing from the spirit of this invention.

The excitation source and optics 16 and detection optics 18 can be mounted in a stationary position, where a multiplicity of reaction vessels with the total internal reflection elements are brought into alignment with the excitation and detection optics at periodic intervals. Those skilled in the art can design thermal cycling carousels (not shown) or X-Y arrays (not shown) such that the TIR elements of the respective reaction units are appropriately aligned with the optics. Alternatively, the excitation and detection optics can be located on a moving platform, preferably under microprocessor control, which aligns with each individual reaction vessel kept in a stationary position.

E. Other Embodiments

Figure 3:
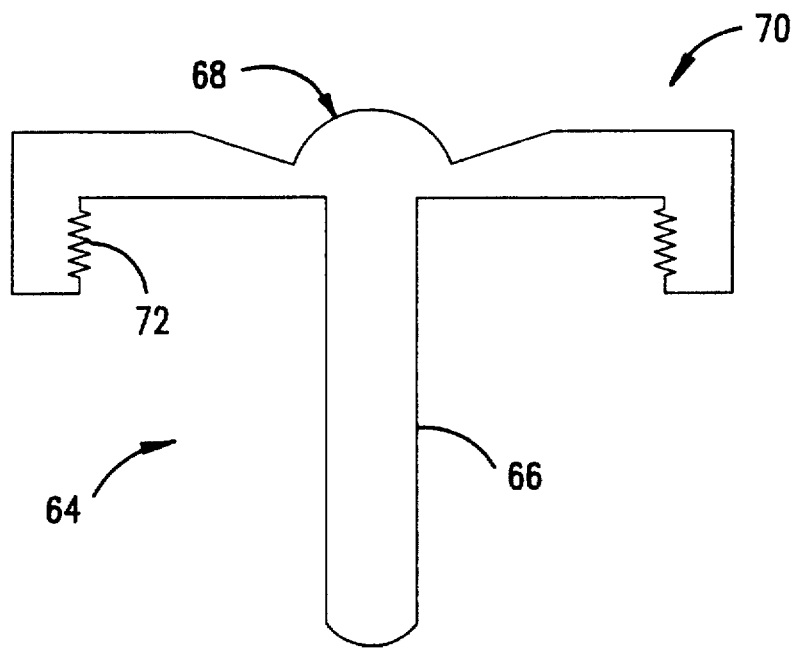
FIG. 3 illustrates a unitary fused embodiment comprising a cylindrical total internal reflection element, a lens therefor, and a reaction chamber seal

FIG. 3 illustrates a fused lens TIR element 64. The TIR element 64 comprises a polished cylindrical rod 66, which is made of high refractive index material. At one end of the rod 66 is a semispherical lens 68 that can be glued to the rod 66, or preferably molded as an integral extrusion of the rod 66. In addition, a sealing member 70 having threads 72 is provided. The sealing member 70 is preferably formed as an extension of the semispherical lens 68. Ideally, the rod 66, lens 68 and sealing member 70 are all formed as one piece of the same material, such as by injection molding. The threads 72 on the sealing member 70 allow the TIR element 64 to be placed in and secured to a reaction vessel (not shown). Attached to the surface of the rod 66 are coupling sites as described above.

Figure 4:
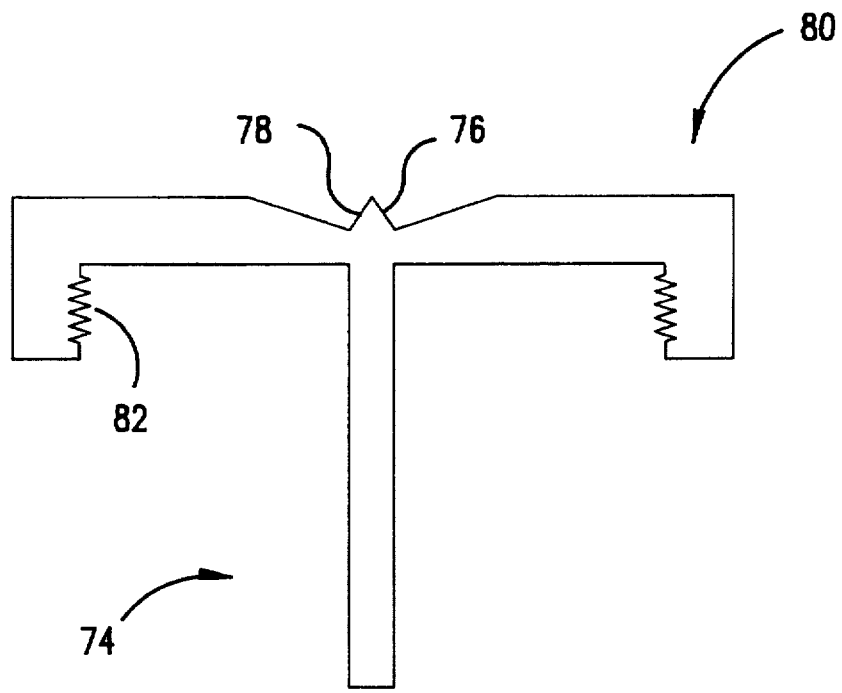
FIG. 4 illustrates a unitary fused embodiment comprising a planar or flat total internal reflection element, a beveled prismatic lens therefor, and a reaction chamber seal

FIG. 4 illustrates a flat or planar TIR element 74 in accordance with another embodiment of the present invention. The TIR element 74 has a beveled entrance surface 76 and exit surface 78 for the excitation and emission beams respectively, thus eliminating the need for a dichroic beamsplitting mirror. A sealing member 80 having threads 82 is provided. The sealing member 80 is preferably formed as an extension of the TIR element 74. More preferably, the TIR element 74 and the sealing member 80 are formed as one piece of the same material, such as by injection molding. The threads 82 on the sealing member 80 allow the TIR element 74 to be placed in and secured to a reaction vessel (not shown). Attached to the surface of the TIR element 74 are coupling sites as described above.

In the embodiments of both FIGS. 3 and 4, it is preferred to block the light from leaving the element and exciting the bulk solution via the end face. For this purpose, a black or highly reflective coating is used as described above. Integral TIR elements of this nature may easily be constructed by injection molding techniques using transparent polymeric materials described above. The formation of these "tapered" TIR elements is described by Lackie, et al., "Instrumentation for Cylindrical Waveguide Evanescent Fluorosensors" in *Biosensors with Fiberoptic Ends*, Wise, et al., eds, The Humana Press, Inc. Clifton, N.J. (1991).

Both cylindrical and planar TIR elements and the ray trace-through have been described by Muller "Spectroscopy with the Evanescent Wave in the Visible Region of the Spectrum" in *Multichannel Image Dectector*, Talmi, Editor, American Chemical Society Symposium Series #102, (1979). The use of flat TIR elements with beveled or prismatic ends has been described in Plate, et al., "Immunoassay Kinetics at Continuous Surfaces", in *Biosensors with Fiberoptic Ends*, supra.

In accordance with another preferred embodiment of the present invention, total internal reflection (TIR) is used to detect target nucleic acid in a reaction vessel by a degradative process rather than a target amplification process. This reaction may be viewed as signal amplification, however, to the extent signal amplification occurs when each molecule of target can be responsible for multiple events which cause a change in signal. The apparatus used for detecting the target nucleic acid is substantially the same as shown in FIGS. 1–4 and the same numerical references will made to that apparatus although the present embodiment employ an amplification reaction. A reaction vessel 20, sealing member 22, and TIR element 24 are provided as described above. In the interior of the reaction vessel 20, the TIR element 24 is exposed to a reaction sample 36. The reaction sample 36 contains the same buffers and sample components as before.

However, the enzymatic reagents and procedure differ in this embodiment. A capture initiator, having a portion of nucleotide sequences which are capable of hybridizing with the target nucleic acid, is bound to the element 24 by any of the methods described above, preferably covalently. The label initiator, having nucleotide sequences which hybridize with an adjacent segment of target, starts out linked to the capture initiator by a scissile linkage, such that the label is within the penetration depth. Methods of coupling molecules using scissile linkages are known in the an and are described in U.S. Pat. Nos. 4,876,187 and 5,011,769 (Meiogenics), which are incorporated herein by reference. As described therein, a scissile linkage is a connecting chemical structure which joins two nucleic acid sequences and which is capable of being selectively cleaved in the presence of an appropriate enzyme and complementary target strands without cleavage of the nucleic acid sequences to which it is joined. Examples of scissile linkage include, but are not limited to, RNA, DNA, amino acid sequences, and carbohydrate polymers such as cellulose or starch. The reaction sample is then treated under conditions sufficient to hybridize the linked initiator sequences and target nucleic acid, if present in the reaction sample.

An agent capable of cleaving the scissile linkage when it is hybridized to target is also present in the reaction sample. For instance, if the scissile linkage is an RNA sequence, an RNase is present in the reaction sample. It is within the skill in the an to determine empirically the types of agents needed to cleave certain scissile linkages, as well as the amount of agent to be added to the reaction sample. As the agent cleaves the scissile linkage, the fluorescing label initiator is free to dissociate from the TIR element 24 and move outside of the penetration depth. During the course of the cleavage reaction, a change (decrease) in fluorescence may be detected using the total internal reflection techniques described above as a measure of the presence and concentration of target nucleic acid present in the reaction sample 36.

In accordance with yet another embodiment of the present invention, an improved method and apparatus for performing TIR detection of specific binding assays, including immunoassays, to detect or quantitate a target molecule or analyte using total internal reflection and differential temperature cycling are provided. As referenced in the "Background Description" section above, immunoassays using total internal reflection techniques are known in the art. Such immunoassays typically detect the presence of diverse target molecules of interest such as haptens, antigens and antibodies in reaction samples.

The apparatus used for performing the immunoassay is substantially the same as shown in FIGS. 1–2 and the same numerical references will made to that apparatus although the present embodiment need not employ a nucleic acid amplification reaction. A reaction vessel 20, a sealing member 22, and TIR element 24 are provided as discussed above. Alternatively, the integral element and sealing means shown in FIGS. 3 and 4 may be used in this embodiment. In the interior of the reaction vessel 20 a TIR element 24 is exposed to a reaction sample 36.

However, the reaction vessel or cell 20 of the present invention is considerably different from the TIR vessels of the prior art. As mentioned in the "Background Description", prior art vessels consisted of flow cells or capillary devices due to the need to minimize diffusion distances. By contrast, the present reaction vessel is termed a "static-volumetric" cell. The modifier "static" is selected because the cell is sealed or closed to other chambers; there is no flow into or out of the cell as in prior an flow cells. The modifier "volumetric" is selected because the cell encompasses a greater volume than a capillary tube. Shapes that are "volumetric" include spheres, cylinders, cubes and the like. Perhaps more importantly,"volumetric" is used to define a relationship between the element surface and the vessel wall that is not conducive to and even prohibits capillary migration. Capillary TIR systems utilize the capillary migration of the fluid to flow across the element. Capillary migration is dependent on the surface tension of the fluid, the distance between the walls of the channel and the hydrophilicity of the wall surfaces For aqueous solutions using a wettable glass element and vessel, a distance of 1.5 mm or less between channel walls is essential to permit capillary action. This distance increases as the surface tension of the sample decreases or as the hydrophilicity of the channel walls increases. Thus, preferred volumetric cells made of glass or similar wettable materials have channel sizes of 1.7 mm or more, preferably 2.0 mm or more. Thus, the term "static-volumetric" excludes the prior an flow cells and capillary tubes.

The reaction sample 36 may comprise various specific binding reagents known in the an and preferably includes a target molecule. The target molecule may be, for example, a nucleic acid, an antigen or hapten, an immunoglobulin, or any other protein of interest. The assay is performed using the TIR element 24 as a solid support for immobilizing reaction sample 36 components. Those persons skilled in the art will be able to determine appropriate assay configurations (e.g. sandwich or competitive) and select appropriate reaction sample 36 components (e.g. anti-analyte antibodies) which may be conjugated to a fluorophore. The prior an provides much guidance in this regard.

The assay is performed while the reaction vessel 20 is exposed to differential temperature cycling. It will be apparent to those skilled in the an that temperatures applied to the reaction vessel 20 should be selected in view of the temperature sensitivity requirements of the reaction sample 36 components and target molecule. For instance, if the target molecule is an immunoglobulin, excessive temperatures, either low or high, should not be applied so as to avoid adverse affects on the target. Nevertheless, cycling of temperature within tolerable ranges is acceptable and within the scope of the present invention. The binding assay temperature may be controlled manually or regulated automatically by a thermal cycler device.

Without intending to limited by any particular theory of operation, it is believed that temperature cycling promotes efficient diffusion of the reaction sample to and from the surface 38 of the TIR element 24. It is also believed that the differential temperature cycling induces convection currents in the fluid medium, and that the convection currents enhance the diffusion of target molecules in the reaction sample to the TIR element surface 38, and thus enhance binding and detection of fluorescent signals. In this manner, a "static-volumetric" cell can be used for TIR detection of a binding assay.

It should also be realized that this temperature cycling provides for additional diffusion (and benefit) in nucleic acid amplification reactions such as PCR and LCR, but neither is essential to the other. In other words, the nucleic acid embodiment can operate without temperature cycling and without a "static-volumetric" cell, but these are both preferments for amplification. Similarly, the "static-volumetric" cell embodiment is not dependent on amplification, or even on nucleic acids for that matter, but they are preferments for this embodiment.

The invention will now be further described by way of examples. The examples are intended to be illustrative only; the invention is limited only by the appended claims.

EXAMPLES

Example 1

Synthesis of Initiator Sequences

Initiator sequences are synthesized according to standard protocols using β cyanoethylphosphoramidite chemistry and a model 380B DNA synthesizer (Applied Biosystems, Foster City, Calif.). Various initiators are provided below in Table 3, as well as in the SEQUENCE LISTING of the present application, where A=adenosine, C=cytidine, G=guanosine, T=thymidine, M=aminomodifier 2™, which introduces a primary amine residue (Clontech, Palo Alto, Calif.), and F=fluorescein (fluorescein phosphoramidite, Peninsula Laboratories, Belmont, Calif.). The PCR and LCR sequences identified, when used in PCR or LCR respectively, will amplify or capture by hybridization, portions of the L1 region of human papilloma virus (HPV). These PCR and LCR probes are disclosed in co-pending, co-owned applications Ser. Nos. 07/589,948, 07/590,105 and/or 07/590,253 all filed Sep. 28, 1990.

sodium carbonate buffer (0.1M $Na_2CO_3$, pH 9.0) to a concentration of 16 μM ($1 \times 10^{15}$ molecules/100 μl). 50 μl aliquots of the initiator are then mixed with 50 gL of a solution of 0.02M 1-3-ethyl-3-(3-dimethylaminopropyl)carbodiimide (EDAC) and incubated overnight at room temperature with that portion of the TIR element 24 (FIG. 1) which protrudes into the reaction sample 36, in order to couple the aminated 5' (initiators 3, 4, 5, 6, 10 and 11) or Y (initiator 13 and 14) end of the initiator sequence to the TIR element. Each TIR element is washed 3–5 times with a stream of water to remove uncoupled initiator sequences.

Example 3

Coupling of Initiator to Glass TIR Element

Glass elements made from commercially available glass rods are chemically derivatized utilizing 3-amino propyl triethoxysilane (Aldrich Chemical Company) in 1% methanol-0.001% 1M hydrochloric acid with oven heating at 75°–100° C. overnight. TIR elements are then rinsed in 0.1M sodium phosphate buffer pH 7.5 followed by 3–4 rinsings in distilled water and are air dried. The derivatized glass TIR elements are then reacted with succinic anhydride for 20–60 minutes to provide a linkage site for initiator sequences. Initiator sequence 3, 4, 5, 6, 10, 11, 13, or 14 (described in Table 3, Example 1) is separately dissolved in 0.1M sodium phosphate buffer, pH 7.5, to a concentration of 32 μM ($2 \times 10^{15}$ molecules/100 μl). That portion of the TIR element 24 (FIG. 1 ) which protrudes into the reaction sample 36 is immersed in 100 μl of a solution of 0.02 μM 1-3-ethyl-3-(3-dimethylaminopropyl)-carbodiimide (EDAC) in phosphate buffer for 30 minutes at room temperature, and 100 μl of initiator is then added. Incubation proceeds overnight at room temperature to couple the ami-

TABLE 3

| Sequence ID. NO. | Sequence Name | DNA Sequence |
|---|---|---|
| 1 | PCR1 | 5'-CGTTTTCCATATTTTTTTGCAGATG-3'(SEQ ID NO. 1) |
| 2 | PCR2 | 5'-FAATTGTACCCTAAATACCCTATATTG-3'(SEQ ID NO. 2) |
| 3 | PCR3 | 5'-MCGTTTTCCATATTTTTTTGCAGATG-3'(SEQ ID NO. 3) |
| 4 | PCR4 | 5'-MTTTTTTTTTTTTTTTTTTTTTCGTTTTCCATATTTTTTTGCAGATG-3'(SEQ ID NO 4) |
| 5 | capture initiator 1 | 5'-MAAGTTGTAAGCACCGATGAATATGT-3'(SEQ ID NO. 5) |
| 6 | capture initiator 2 | 5'-MTTTTTTTTTTTTTTTTTTTTTAAGTTGTAAGCACCGATGAATATGT-3'(SEQ ID NO. 6) |
| 7 | LCR1 | 5'-ACATATTCATCCGTGCTTACAACT-3'(SEQ ID NO. 7) |
| 8 | LCR2 | 5'-TGCACGCACAAACATATATTATCAF-3'(SEQ ID NO. 8) |
| 9 | LCR3 | 5'-FATGATAATATATGTTTGTGCGTGCA-3'(SEQ ID NO. 9) |
| 10 | LCR4 | 5'-MAAGTTGTAAGCACGGATGAATATGT-3'(SEQ ID. NO. 10) |
| 11 | LCR5 | 5'-MTTTTTTTTTTTTTTTTTTTTTAAGTTGTAAGCACGGATGAATATGT-3'(SEQ ID NO. 11) |
| 12 | LCR6 | 5'-GCGGACAGGCGGAAGTTGTAAGCACGGATGAATATGT-3'(SEQ ID NO. 12) |
| 13 | capture initiator 3 | 5'-CCGCCTGTCCGCM-3'(SEQ ID NO. 13) |
| 14 | capture initiator 4 | 5'-CCGCCTGTCCGCTTTTTTTTTTTTTTTTTTTTM-3'(SEQ ID NO. 14) |

Example 2

Coupling of Initiator to Styrene Maleic Anhydride TIR Element

Chemically activated TIR elements are prepared as described in the specification above using styrene maleic anhydride (commercially available from ARCO Chemical Company). Initiator sequence 3, 4, 5, 6, 10, 11, 13, or 14 (described in Table 3, Example 1) is separately dissolved in nated 5' or 3' end of the sequence to the TIR element as in the previous example. Each TIR element is washed 3–5 times with a stream of water to remove uncoupled initiator sequences.

Example 4

PCR Using Initiator Coupled to TIR Element

Reaction units 14 (FIG. 1) are assembled comprising TIR elements 24 with PCR3 (described in Table 3, Example 1)

covalently attached, and the reaction vessels 20. The following reagents are added to each reaction vessel 20 to a total volume of 100 μl, at 90° C.: 1 pmole PCR2; 1 unit *Thermus thermophilus* DNA polymerase; 100 nmole each dATP, dCTP, dGTP, and dTTP; and either 1 ng human placental DNA or a sample containing approximately 1 ng of Human Papilloma Virus DNA; all in a buffer of 100 nM NaCl, 50 mM MgCl$_2$, pH 8.0. PCR proceeds essentially as described by Saiki, et al., *Science*, 230:1350–1354 (1985). The reaction vessels 20 are subjected to 35 cycles of alternating temperature: 1 minute at 94° C., 1 minute at 65° C., and 2.5 minutes at 72° C. Following PCR, the reaction vessels 20 are cooled to 25° C., and the fluorescence along the TIR elements is measured.

Example 5

PCR Using Initiator Coupled to TIR Element by poly T Spacer

Reaction units are assembled and PCR is performed as described in Example 4 above, except that PCR4 (described in Table 3, Example 1) is covalently attached to TIR elements. PCR4 consists of a 3' segment identical to PCR3 that is coupled to a 5' spacer segment of poly T. Following PCR, the reaction vessels are cooled to 25° C., and the fluorescence along the TIR elements is measured.

Example 6

PCR Using Capture Initiator Coupled to TIR Element

Reaction units are assembled and PCR is performed as described in Example 4 above, except that capture initiator 1 (described in Table 3, Example 1) is covalently attached to TIR elements. The reaction sample is as in Example 4, except 1 pmole PCR1 is also added. The PCR proceeds with PCR 1 and PCR2 as initiator pairs for 35 cycles as described in Example 4. Following PCR, the reaction vessels are cooled to 25° C., resulting in hybridization of capture initiator 1 to the fluorescein-labeled (−) strand of the amplicon. The fluorescence along the TIR elements is then measured.

Example 7

PCR Using Capture Initiator Coupled to TIR Element by poly T Spacer

Reaction units are assembled as described in Example 4 above, except that capture initiator 2 (described in Table 3, Example 1) is covalently attached to TIR elements. Capture initiator 2 is identical to capture initiator 1 except that it is coupled to a poly T spacer segment. The reaction sample is as in Example 6, and PCR proceeds for 35 cycles as described in Example 4. Following PCR, the reaction vessels are cooled to 25° C., resulting in hybridization of the 25-base HPV recognition portion of capture initiator 2 to the fluorescein-labeled (−) strand of the amplicon. The fluorescence along the TIR elements is then measured.

Example 8

LCR Using Initiators Coupled to TIR Element

Reaction units are assembled as described in Example 4 above, except that LCR4 (described in Table 3, Example 1) is covalently attached to TIR elements. The reaction sample includes 1700 units *Thermus thermophilus* DNA ligase, 10 μM NAD, 0.1 pmole each initiator sequence LCR1, LCR2, and LCR3 in a buffer comprising 50 mM N-(2-hydroxyethyl)piperazine-N'-(3-propanesulfonic acid) (EPPS), 30 mM MgCl$_2$, 0.01% bovine serum albumin, pH 8.0. The reaction sample is assembled at 85° C. The ligase chain reaction (LCR) proceeds essentially as described by Backman and Wang [EP-A-320 308 (1988)]. The reaction vessels are subjected to 35 cycles of alternating temperature: 1 minute at 85° C. and 1.5 minute at 50° C. Following LCR, the reaction vessels are cooled to 25° C. and the fluorescence along the TIR elements is measured.

Example 9

LCR Using Initiator Coupled to TIR Element by poly T Spacer

Reaction units are assembled as described in Example 4 above, except that LCR5 (described in Table 3, Example 1) is covalently attached to TIR elements. LCR5 consists of a 3' segment identical to LCR4 that is coupled to a 5' spacer segment of poly T. The reaction sample is assembled and LCR is performed as in Example 8. Following LCR, the reaction vessels are cooled to 25° C., and the fluorescence along the TIR elements is measured.

Example 10

LCR Using Capture Initiator Coupled to TIR Element

Reaction units are assembled as described in Example 4 above, except that capture initiator 3 (described in Table 3, Example 1) is covalently attached to TIR elements. The reaction sample is as in Example 8 above, except 0.1 pmole LCR6 is also added. LCR6 consists of a 3' segment identical to LCR4 that is coupled to a 5' segment complementary to and hybridizable with capture initiator 3. LCR proceeds for 35 cycles as described in Example 8. Following LCR, the reaction vessels are cooled to 25° C., resulting in hybridization of the 12-base single-stranded segment of LCR6 to the capture initiator coupled to the surface of the TIR element. The fluorescence along the TIR elements is then measured.

Example 11

LCR Using Capture Initiator Coupled to TIR Element by poly T Spacer

Reaction units are assembled as described in Example 4 above, except that capture initiator 4 (described Table 3, Example 1) is covalently attached to TIR elements. Capture initiator 4 is identical to capture initiator 3 except for a poly T spacer segment at the element (aminated) end. The reaction sample is as in Example 10. The LCR proceeds for 35 cycles as described in Example 8. Following LCR, the reaction vessels are cooled to 25° C., resulting in hybridization of the 12-base single-stranded tail of LCR6 to the 12-base tail-complementary portion of capture initiator 4 coupled to the surface of the TIR element. The fluorescence along the TIR elements is then measured.

While the invention has been shown and described in connection with particular preferred embodiments, it will be apparent that certain changes and modifications, in addition to those mentioned above, may be made by those who are skilled in the art without departing from the basic features of the present invention. Accordingly, it is the intention of the Applicants to protect all variations and modifications within the true spirit and valid scope of the invention.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CGTTTTCCAT ATTTTTTTGC AGATG        25

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1

( x i ) SEQUENCE DESCRIPTION: SEQ ID NO:2:

AATTGTACCC TAAATACCCT ATATTG        26

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1

( x i ) SEQUENCE DESCRIPTION: SEQ ID NO:3:

CGTTTTCCAT ATTTTTTTGC AGATG        25

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1

( x i ) SEQUENCE DESCRIPTION: SEQ ID NO:4:

TTTTTTTTTT TTTTTTTTTT CGTTTTCCAT ATTTTTTTGC AGATG    45

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1

( x i ) SEQUENCE DESCRIPTION: SEQ ID NO:5:

AAGTTGTAAG CACCGATGAA TATGT    25

( 2 ) INFORMATION FOR SEQ ID NO:6:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1

( x i ) SEQUENCE DESCRIPTION: SEQ ID NO:6:

TTTTTTTTTT TTTTTTTTTT AAGTTGTAAG CACCGATGAA TATGT    45

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

ACATATTCAT CCGTGCTTAC AACT    24

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 24

( x i ) SEQUENCE DESCRIPTION: SEQ ID NO:8:

TGCACGCACA AACATATATT ATCA    24

( 2 ) INFORMATION FOR SEQ ID NO:9:

( i ) SEQUENCE CHARACTERISTICS:
        ( A ) LENGTH: 25 base pairs
        ( B ) TYPE: nucleic acid (C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1

(xi) SEQUENCE DESCRIPTION: SEQ ID NO:9:

ATGATAATAT ATGTTTGTGC GTGCA 25

(2) INFORMATION FOR SEQ ID NO:10:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1

(xi) SEQUENCE DESCRIPTION: SEQ ID NO:10:

AAGTTGTAAG CACGGATGAA TATGT 25

(2) INFORMATION FOR SEQ ID NO:11:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1

(xi) SEQUENCE DESCRIPTION: SEQ ID NO:11:

TTTTTTTTTT TTTTTTTTTT AAGTTGTAAG CACGGATGAA TATGT 45

(2) INFORMATION FOR SEQ ID NO:12:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

GCGGACAGGC GGAAGTTGTA AGCACGGATG AATATGT 37

(2) INFORMATION FOR SEQ ID NO:13:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 12

( x i ) SEQUENCE DESCRIPTION: SEQ ID NO:13:

CCGCCTGTCC GC 1 2

( 2 ) INFORMATION FOR SEQ ID NO:14:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: misc_feature
      ( B ) LOCATION: 32

( x i ) SEQUENCE DESCRIPTION: SEQ ID NO:14:

CCGCCTGTCC GCTTTTTTTT TTTTTTTTT TT 3 2

What is claimed is:

1. A method of detecting amplified target nucleic acid using total internal reflection, comprising the steps providing a closed static-volumetric reaction vessel having disposed therein (a) reaction sample, containing the target nucleic acid, (b) a total internal reflection (TIR) element, (c) a plurality of members of at least one initiator sequence set and reagents for producing amplification of target nucleic acid present in the reaction sample, (d) label means which is coupled to a fluorophore, and (e) capture means for bringing said fluorophore within the penetration depth of said element, wherein said label means or said capture means is specific for said target nucleic acid;

producing an evanescent electromagnetic wave in the TIR element which penetrates into the reaction sample adjacent the element and has an associated penetration depth;

reacting the reaction sample, the members of said initiator sequence set and amplification reagents under conditions sufficient to amplify target nucleic acid present in the reaction sample to produce amplification products wherein said amplification products are labeled with said label means during amplification or said amplification products are labeled with said labels means by contacting said amplification products with a specific binding member attached to a label;

capturing said label amplification products within the penetration depth as a function of the presence or amount of target nucleic acid; and detecting within the TIR element a change in fluorescence as a measure of target nucleic acid to thereby amplify and detect said target sequence in said closed static-volumetric reaction vessel.

2. The method of claim 1 wherein at least one member of the initiator sequence set is coupled to a specific binding member which serves also as the capture means or label means.

3. The method of claim 2 wherein said specific binding member comprises a hapten and either the capture means further comprises antihapten antibody immobilized on the element, or the label means further comprises antihapten conjugated to a fluorophore.

4. The method of claim 2 wherein said specific binding member comprises a polynucleotide tail and either the capture means further comprises a complementary polynucleotide tail immobilized on the element, or the label means further comprises a complementary polynucleotide tail conjugated to a fluorophore.

5. The method of claim 1 wherein at least one member of the initiator sequence set is coupled to the TIR element by covalent bonding.

6. The method of claim 5 wherein said at least one member of an initiator sequence set is coupled to the TIR element via a spacer molecule.

7. The method of claim 1 wherein a capture probe complementary to a portion of the amplified target is immobilized on said TIR element.

8. The method of claim 1 wherein the reaction sample, initiator sequence sets and amplification reagents are reacted under thermal cycling conditions.

9. The method of claim 8 wherein the amplification reagents include an enzymatic agent that induces amplification, said enzymatic agent selected from thermostable DNA polymerase, thermostable DNA ligase or a combination thereof.

10. The method of claim 9 wherein the target nucleic acid present in the reaction sample is amplified by polymerase chain reaction or ligase chain reaction.

11. The method of claim 1 wherein the reaction sample, initiator sequence sets and amplification reagents are reacted under isothermal conditions.

12. The method of claim 1 wherein the step of producing an evanescent wave adjacent to the TIR element comprises directing a beam emitted by an excitation source onto the TIR element and totally internally reflecting the beam in the TIR element.

13. A method of detecting target nucleic acid in a reaction vessel using total internal reflection, comprising the steps of:

providing a closed static-volumetric reaction vessel having disposed therein (a) a reaction sample, (b) a total internal reflection (TIR) element, (c) a plurality of members of an initiator sequence, each sequence comprising a capture segment linked to a label segment by a scissile linkage, wherein said initiator includes a portion of nucleotide sequences which are capable of hybridizing with the target nucleic acid, and wherein said label segment is coupled to a fluorophore, and (d) means for cleaving the scissile linkage when target is hybridized to the initiator;

producing an evanescent electromagnetic wave in the TIR element which penetrates into the reaction sample adjacent the element and has an associated penetration depth, and detecting in the TIR element the fluorescence resulting from the linked fluorophore present within the penetration depth;

reacting the reaction sample, initiator sequences and means for cleaving under conditions sufficient to (a) hybridize target nucleic acid present in the reaction sample to the initiator sequences, and (b), in the presence of target, cleave the scissile linkage, thereby freeing the fluorophore from the penetration depth; and detecting in the TIR element a change in fluorescence as a measure of target nucleic acid to thereby react and detect said target nucleic acid in said closed static-volumetric reaction vessel.

* * * * *

UNITED STATES PATENT AND TRADEMARK OFFICE
CERTIFICATE OF CORRECTION

PATENT NO. : 5,585,242
DATED : December 17, 1996
INVENTOR(S) : Bouma, et. Al.

It is certified that error appears in the above-indentified patent and that said Letters Patent is hereby corrected as shown below:

Column 29, line 25, change "steps" to --steps of:--.

Column 29, line 27, change "(a)" to --(a) a--.

Column 29, line 27, change "sample," to --sample--.

Column 29, line 50, change "label" to --labeled--.

Signed and Sealed this

Twenty-ninth Day of April, 1997

Attest:

BRUCE LEHMAN

*Attesting Officer*  *Commissioner of Patents and Trademarks*